(12) United States Patent
Kasper

(10) Patent No.: US 12,734,284 B2
(45) Date of Patent: Sep. 15, 2026

(54) SYSTEM AND METHOD FOR CREATING CELL PROCESSING PROTOCOLS

(71) Applicant: Haemonetics Corporation, Boston, MA (US)

(72) Inventor: Seth Kasper, Orleans, MA (US)

(73) Assignee: HAEMONETICS CORPORATION, Boston, MA (US)

( * ) Notice: Subject to any disclaimer, the term of this patent is extended or adjusted under 35 U.S.C. 154(b) by 0 days.

(21) Appl. No.: 17/274,251

(22) PCT Filed: Sep. 11, 2019

(86) PCT No.: PCT/US2019/050539
§ 371 (c)(1),
(2) Date: Mar. 8, 2021

(87) PCT Pub. No.: WO2020/055958
PCT Pub. Date: Mar. 19, 2020

(65) Prior Publication Data

US 2021/0353846 A1 Nov. 18, 2021

Related U.S. Application Data

(60) Provisional application No. 62/729,952, filed on Sep. 11, 2018.

(51) Int. Cl.
*A61M 1/36* (2006.01)
*A61M 1/34* (2006.01)
(Continued)

(52) U.S. Cl.
CPC ........ *A61M 1/3692* (2014.02); *A61M 1/3496* (2013.01); *A61M 1/3693* (2013.01);
(Continued)

(58) Field of Classification Search
CPC .............. A61M 1/3692; A61M 1/3496; A61M 1/3693; A61M 2202/0429;
(Continued)

(56) References Cited

U.S. PATENT DOCUMENTS 3,645,252 A 2/1972 Gilford
3,655,123 A 4/1972 Judson et al.
(Continued)

FOREIGN PATENT DOCUMENTS

CA 2840901 A1 1/2013
EP 0223126 A2 5/1987
(Continued)

OTHER PUBLICATIONS

Cell Saver Elite User Manual, Haemonetics Corporation, Part No. 120745-US(AA), Jun. 2016.*
(Continued)

*Primary Examiner* — Claire X Wang
*Assistant Examiner* — Shuyi S. Liu
(74) *Attorney, Agent, or Firm* — McCarter & English, LLP; Jonathan C. Lovely

(57) ABSTRACT

A method for creating a custom cell processing protocol includes providing a cell processing device having a display, a blood component separation device, and a pump. The method may then select, using the display, a first and second processing phase. The first processing phase has a plurality of first processing phase parameters and the second processing phase has a plurality of second processing phase parameters. The method may then modify the first and second processing phase parameters using the display, and create a custom protocol algorithm. The algorithm may be based, at least in part, on the selected first and second processing phases and the modified first and second processing phase parameters.

10 Claims, 13 Drawing Sheets

(51) Int. Cl.
*B04B 5/04* (2006.01)
*B04B 13/00* (2006.01)
*G05B 13/02* (2006.01)
*G16H 40/40* (2018.01)
*G16H 40/63* (2018.01)

(52) U.S. Cl.
CPC ............ *B04B 5/0442* (2013.01); *B04B 13/00* (2013.01); *G05B 13/0265* (2013.01); *G16H 40/40* (2018.01); *G16H 40/63* (2018.01); *A61M 2202/0429* (2013.01); *A61M 2205/50* (2013.01); *A61M 2205/505* (2013.01)

(58) Field of Classification Search
CPC ........ A61M 2205/50; A61M 2205/505; A61M 1/0281; A61M 1/385; B04B 5/0442; B04B 13/00; G05B 13/0265; G16H 40/40; G16H 40/63; A61B 5/150221; A61B 5/150229; A61B 5/155; A61B 5/157; A61B 5/15003
USPC ........................................ 494/1, 2, 3, 4, 5, 6
See application file for complete search history.

(56) References Cited

U.S. PATENT DOCUMENTS 3,768,653 A 10/1973 Brumfield
3,965,896 A 6/1976 Swank
4,033,345 A 7/1977 Sorenson et al.
4,049,192 A 9/1977 Krebs et al.
4,054,523 A 10/1977 Ingenito et al.
4,086,924 A 5/1978 Latham, Jr.
4,115,277 A 9/1978 Swank
4,151,844 A 5/1979 Cullis et al.
4,189,470 A 2/1980 Rose
4,236,960 A 12/1980 Hultman et al.
4,243,531 A 1/1981 Crockett et al.
4,321,192 A 3/1982 Jain
4,411,786 A 10/1983 Russell
4,416,654 A 11/1983 Schoendorfer et al.
4,482,342 A 11/1984 Lueptow et al.
4,531,954 A 7/1985 Klein
4,561,868 A 12/1985 von Reis et al.
4,668,214 A 5/1987 Reeder
4,673,423 A 6/1987 Yumlu
4,680,025 A 7/1987 Kruger et al.
4,681,677 A 7/1987 Kuh et al.
4,704,203 A 11/1987 Reed
4,743,371 A 5/1988 Servas et al.
4,758,337 A 7/1988 Kohn et al.
4,781,707 A 11/1988 Boehringer et al.
4,795,448 A 1/1989 Stacey et al.
4,806,252 A 2/1989 Brown et al.
4,828,543 A 5/1989 Weiss et al.
4,828,716 A 5/1989 McEwen et al.
4,834,890 A 5/1989 Brown et al.
4,872,988 A 10/1989 Culkin
4,886,487 A 12/1989 Solem et al.
4,898,572 A 2/1990 Surugue nee Lasnier et al.
4,919,817 A 4/1990 Schoendorfer et al.
4,943,273 A 7/1990 Pages
4,946,434 A 8/1990 Plaisted et al.
4,954,251 A 9/1990 Barnes et al.
5,015,388 A 5/1991 Pusineri et al.
5,053,121 A 10/1991 Schoendorfer et al.
5,055,198 A 10/1991 Shettigar
5,076,911 A 12/1991 Brown et al.
5,133,703 A 7/1992 Boehringer et al.
5,135,645 A 8/1992 Sklenak et al.
5,147,290 A 9/1992 Jonsson
5,182,019 A 1/1993 Cote et al.
5,183,569 A 2/1993 Kyriacou
5,215,519 A 6/1993 Shettigar
5,223,154 A 6/1993 MacPherson, Jr. et al.
5,234,403 A 8/1993 Yoda et al.
5,238,655 A 8/1993 Laible et al.
5,294,401 A 3/1994 Hagiwara
5,298,016 A 3/1994 Gordon
5,308,506 A 5/1994 McEwen et al.
5,311,908 A 5/1994 Barone et al.
5,344,570 A 9/1994 McLachlan et al.
5,378,227 A 1/1995 O'Riordan et al.
5,385,539 A 1/1995 Maynard
5,386,734 A 2/1995 Pusinelli
5,411,472 A 5/1995 Steg, Jr. et al.
5,411,705 A 5/1995 Thor et al.
5,417,650 A 5/1995 Gordon
5,419,759 A 5/1995 Naficy
5,423,738 A 6/1995 Robinson et al.
5,458,566 A 10/1995 Herrig et al.
5,464,399 A 11/1995 Boettger
5,478,479 A 12/1995 Herrig
5,554,293 A 9/1996 Uhoch
5,634,893 A 6/1997 Rishton
5,643,193 A 7/1997 Papillon et al.
5,651,766 A 7/1997 Kingsley et al.
5,658,256 A 8/1997 Shields
5,674,173 A 10/1997 Hlavinka et al.
5,725,777 A 3/1998 Taylor
5,733,253 A 3/1998 Headley et al.
5,770,073 A 6/1998 Bach et al.
5,800,721 A 9/1998 McBride
5,879,624 A 3/1999 Boehringer et al.
5,891,080 A 4/1999 Skinkle et al.
5,954,971 A 9/1999 Pages et al.
5,971,948 A 10/1999 Pages et al.
6,007,472 A 12/1999 Schill et al.
6,250,330 B1 6/2001 Welker
6,251,284 B1 6/2001 Bischof et al.
6,251,291 B1 6/2001 Lamphere et al.
6,267,925 B1 7/2001 Pages
6,464,624 B2 10/2002 Pages
6,508,778 B1 1/2003 Verkaart et al.
6,622,052 B1* 9/2003 Rosiello ............. G05B 19/0426 700/83
6,632,189 B1 10/2003 Fallen et al.
6,632,191 B1 10/2003 Headley et al.
6,723,086 B2 4/2004 Bassuk et al.
6,800,072 B2 10/2004 Patzer
6,890,316 B2 5/2005 Rawles et al.
7,008,393 B2 3/2006 Robinson et al.
7,037,428 B1 5/2006 Robinson et al.
8,016,736 B2 9/2011 Hlavinka et al.
8,157,103 B2 4/2012 Eagle et al.
8,409,125 B2 4/2013 Bobroff
8,628,671 B2 1/2014 Eagle et al.
10,293,097 B2 5/2019 Murphy et al.
10,500,330 B2 12/2019 Schwarz et al.
10,668,207 B2 6/2020 Kasper et al.
2002/0179544 A1 12/2002 Johnson et al.
2005/0203469 A1 9/2005 Bobroff et al.
2008/0058695 A1 3/2008 Perovitch et al.
2008/0124700 A1 5/2008 Fortini et al.
2010/0069215 A1 3/2010 Lee et al.
2010/0280500 A1 11/2010 Skelton et al.
2012/0116347 A1* 5/2012 Weinert ................. G16H 20/10 604/500
2013/0045852 A1 2/2013 Chapman et al.
2013/0197470 A1 8/2013 Bobroff
2014/0128239 A1 5/2014 Murphy et al.
2015/0273132 A1 10/2015 Ragusa et al.
2015/0314060 A1 11/2015 Maculan et al.
2016/0124009 A1* 5/2016 Wasson ............ G01N 35/00871 422/65
2017/0262601 A1 9/2017 Binninger et al.
2017/0326278 A1 11/2017 Camisani et al.
2018/0240322 A1* 8/2018 Potucek .................... E04H 4/14
2019/0231964 A1 8/2019 Uhlmann

FOREIGN PATENT DOCUMENTS

EP 0573117 A1 12/1993
EP 0682953 A1 11/1995

(56) References Cited

FOREIGN PATENT DOCUMENTS

| | | | | | |
|---|---|---|---|---|---|
| EP | 0771570 | A1 | | 5/1997 | |
| EP | 1166806 | | | 1/2002 | |
| EP | 2727615 | B1 | | 11/2015 | |
| EP | 3461511 | B1 | | 4/2022 | |
| GB | 2250699 | A | | 6/1992 | |
| JP | H04-236960 | A | | 8/1992 | |
| JP | 6-315530 | A | | 11/1994 | |
| JP | H11-506030 | A | | 6/1999 | |
| JP | 2005-312903 | A | | 11/2005 | |
| JP | 2008-538514 | A | | 10/2008 | |
| JP | 2011-025069 | A | | 2/2011 | |
| JP | 2013527165 | A | * | 6/2013 | .......... A61M 1/3633 |
| WO | 1984/00892 | A1 | | 3/1984 | |
| WO | 1989/01792 | A1 | | 3/1989 | |
| WO | 1989/04709 | A1 | | 6/1989 | |
| WO | 1994/21311 | A2 | | 9/1994 | |
| WO | 1995/03840 | A1 | | 2/1995 | |
| WO | 1996/40319 | A1 | | 12/1996 | |
| WO | 1998/14163 | A1 | | 4/1998 | |
| WO | 2000/38756 | A1 | | 7/2000 | |
| WO | 2006/100651 | A1 | | 9/2006 | |
| WO | 2017/087774 | A1 | | 5/2017 | |
| WO | 2019/217964 | A1 | | 11/2019 | |

OTHER PUBLICATIONS

Ferraris et al., Perioperative blood transfusion and blood conservation in cardiac surgery: the Society of Thoracic Surgeons and the Society of Cardiovascular Anesthesiologists clinical practice guideline. Ann Thorac Surg. May 2007;83(5 Suppl):S27-86.

International Search Report and Written Opinion for Application No. PCT/US2019/050539, dated Dec. 4, 2019, 12 pages.

* cited by examiner

Settings Screen: Build Screen

Build Fill Phase

Fill Phase Built

Build Wash Phase

Build Empty 1 Phase

Build Rinse Phase

Build Empty 2 Phase

Settings Screen: Full Flex Protocol Test 1 Procedure Built Out Example

Settings Screen Activate Flex Protocol 1

New Protocol, Name First Phase Prime

Build Prime Phase

Build Add Cells Phase (User Volume Input)

Build Wash Phase

Build Empty Phase

Settings Screen Flex Protocol Test 2 Built

Activate Flex Protocol 2. Note: both procedure now available at start-up

SYSTEM AND METHOD FOR CREATING CELL PROCESSING PROTOCOLS

PRIORITY

This patent application is a 35 U.S.C. § 371 national stage filing of International Application No. PCT/US2019/050539, filed on Sep. 11, 2019, which claims priority from U.S. Provisional Application No. 62/729,952, filed on Sep. 11, 2018, entitled "System and Method for Creating Cell Processing Protocols," (formerly 1611/C96), and naming Seth Kasper as inventor. The disclosure of each of the foregoing applications is incorporated herein, in its entirety by reference.

TECHNICAL FIELD

The present invention relates to apheresis and cell processing devices and more particularly to creating custom protocols for apheresis and cell processing devices.

BACKGROUND ART

In many applications it is desirable to drain and collect blood and other fluids from wounds and surgical sites (e.g., intra-operatively and/or post-operatively). Not only does the removal of fluids aid in healing and reduce the threat of infection, when blood is collected, it provides the hospital the opportunity to return the collected blood back to the patient. This, in turn, reduces the need to transfuse blood that is not the patient's own blood (e.g., allogeneic blood).

Prior-art systems typically have one or more set protocols that the device must follow. In some instances, the user may have the ability to select one of the protocols and modify processing speed, wash volume or starting volume, but does not have the ability to customize the protocol beyond the established workflow to a given application and/or use. Therefore, prior art systems may have limited applications outside of their original use.

SUMMARY OF THE EMBODIMENTS

In a first embodiment of the invention, a method for creating a custom cell processing protocol includes providing a cell processing device that has a display, a blood component separation device, and a pump. The method also includes selecting, using the display, a first processing phase that has a plurality of first processing phase parameters, and modifying at least one of the first processing phase parameters using the display. The method may then select, using the display, a second processing phase that has a plurality of second processing phase parameters and modify at least one of the second processing phase parameters using the display. Once the phases are selected and parameters are modified, the method may create a custom protocol algorithm. The protocol algorithm may be based, at least in part, on the selected first and second processing phases and the modified first and second processing phase parameters.

The first processing phase parameters and/or the second processing phase parameters may include a flow direction, valve position, centrifuge speed, pump speed, end point criteria, button press points, effluent levels, bowl optics values, target volumes, phase times, and/or end volume. The first processing phase may be a fill phase or a prime phase. The second processing phase may be a wash phase, an empty phase, a rinse phase and/or an add cell phase.

In some embodiments, the method may also include selecting, using the display, a third processing phase that has a plurality of third processing phase parameters. Additionally, the method may modify at least one of the third processing phase parameters using the display. The custom protocol algorithm may then be based, at least in part, on the selected third processing phases and the modified third processing phase parameters.

The method may include selecting, using the display, a bowl size for the blood component separation device and/or validating the protocol algorithm prior to allowing the user to run the protocol (e.g., by running a simulation of the protocol). Additionally or alternatively, the method may include selecting a pre-set application mode that adjusts at least one of the first or second processing phase parameters. For example, the pre-set application may be a high quality mode, a default mode, and an expedited mode. The pump may operate at a high speed when in the expedited mode and/or a low speed when in the high quality mode.

The method may also include selecting messages to be displayed to the user during operation of cell processing device according to the custom protocol algorithm. Additionally or alternatively, the method may optimize the custom protocol algorithm by running the custom protocol algorithm on the cell processing device and selecting, using the display, thresholds for an end of a given state.

In accordance with further embodiments, a system for creating custom cell processing protocols may include a cell processing device, an interface and a processor. The cell processing device may process blood and/or blood products and may have a blood component separation device and a pump. The interface may be located on the cell processing device and may allow a user to select (1) a first processing phase having a plurality of first processing phase parameters and (2) a second processing phase having a plurality of second processing phase parameters. Additionally, the interface may allow the user to modify at least one of the first processing phase parameters and/or at least one of the second processing phase parameters. The processor may generate a custom protocol algorithm based, at least in part, on the selected first and second processing phases and the modified first and second processing phase parameters.

The system may also include a controller located within the cell processing device. The controller may operate the cell processing device according to the custom protocol algorithm. For example, the controller may control the operation of the blood component separation device and the pump (e.g., according to the custom protocol algorithm). The first and second processing phase parameters may include flow direction, valve position, centrifuge speed, pump speed, end point criteria, button press points, effluent levels, bowl optics values, target volumes, phase times, and/or end volumes. The first processing phase may be a fill phase or a prime phase. The second processing phase may be a wash phase, an empty phase, a rinse phase and/or an add cell phase.

In some embodiments, the interface may also allow a user to (1) select a third processing phase that has third processing phase parameters, and (2) modify at least one of the third processing phase parameters. In such embodiments, the custom protocol algorithm may be based, at least in part, on the selected third processing phases and the modified third processing phase parameters. The interface may also allow the user to select a bowl size for the blood component separation device. The processor may validate the protocol algorithm prior to allowing the user to run the protocol algorithm on the cell processing device. For example, the processor may run a simulation of the protocol to validate the protocol algorithm.

The system may also have a pre-set application mode that adjusts one of the first or second processing phase parameters. For example, the pre-set application mode may be a high quality mode, a default mode, and an expedited mode. The pump may operate at a high speed when in the expedited mode and/or a low speed when in the high quality mode. The interface may include a display and the blood processing device may include a centrifuge bowl. The interface may also allow the user to select messages to be displayed to the user during operation of the cell processing device according to the custom protocol algorithm. Additionally or alternatively, the interface may allow the user to select an end point for at least one given state during operation of the cell processing device according to the custom protocol algorithm to optimize the custom protocol algorithm.

In accordance with further embodiments, a method for creating a custom cell processing protocol includes providing a cell processing device that has a display, a blood component separation device, a plurality of valves and a pump. The method may also include performing a cell processing procedure on the cell processing device and manually controlling the operation of the cell processing device during the cell processing procedure. A processor may monitor the manual control of the operation of the cell processing device during the cell processing procedure and the method may create a custom protocol algorithm based, at least in part, on the monitored manual control of the operation of the cell processing device. Manually controlling the operation of the cell processing device may include manual operation of at least one of the plurality of valves, manual operation of the pump speed, manual operation of process volumes, manual operation of the state the cell processing device is in, and/or manual operation of system parameters. The method may also save the custom protocol algorithm in a data storage device and/or modify the custom protocol algorithm.

In additional embodiments, a system for creating a custom cell processing protocol includes a cell processing device that processes blood and/or blood products. The cell processing device may include a blood component separation device, a plurality of valves, and a pump. The system may also include an interface located on the cell processing device that allows a user to place the cell processing device into a learning mode in which the user may manually control the operation of the cell processing device during a cell processing procedure. A processor may monitor the manual control of the operation of the cell processing device during the cell processing procedure when in the learning mode and may generate a custom protocol algorithm. The custom protocol algorithm may be based, at least in part, on the monitored manual control of the operation of the cell processing device.

The manual control of the operation of the cell processing device may include manual operation of one of the valves, manual operation of the pump speed, manual operation of process volumes, manual operation of the state the cell processing device is in, and/or manual operation of system parameters. The system may have a data storage device that stores the custom protocol algorithm and/or the interface may allow the user to modify the custom protocol algorithm. The cell processing device may have a controller that operates the cell processing device according to the custom protocol algorithm. For example, the controller may control the pump, the blood component separation device, and/or one or more of the valves.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, systems and methods may create custom cell processing protocols for a cell processing device. The user may select, using a display on the cell processing device, one or more processing phases for the protocol and modify some of the phase parameters. Based on the selected processing phases and the modified parameters, the system/method may create a custom protocol algorithm to be run on the cell processing device.

Figures 1A, 1B:
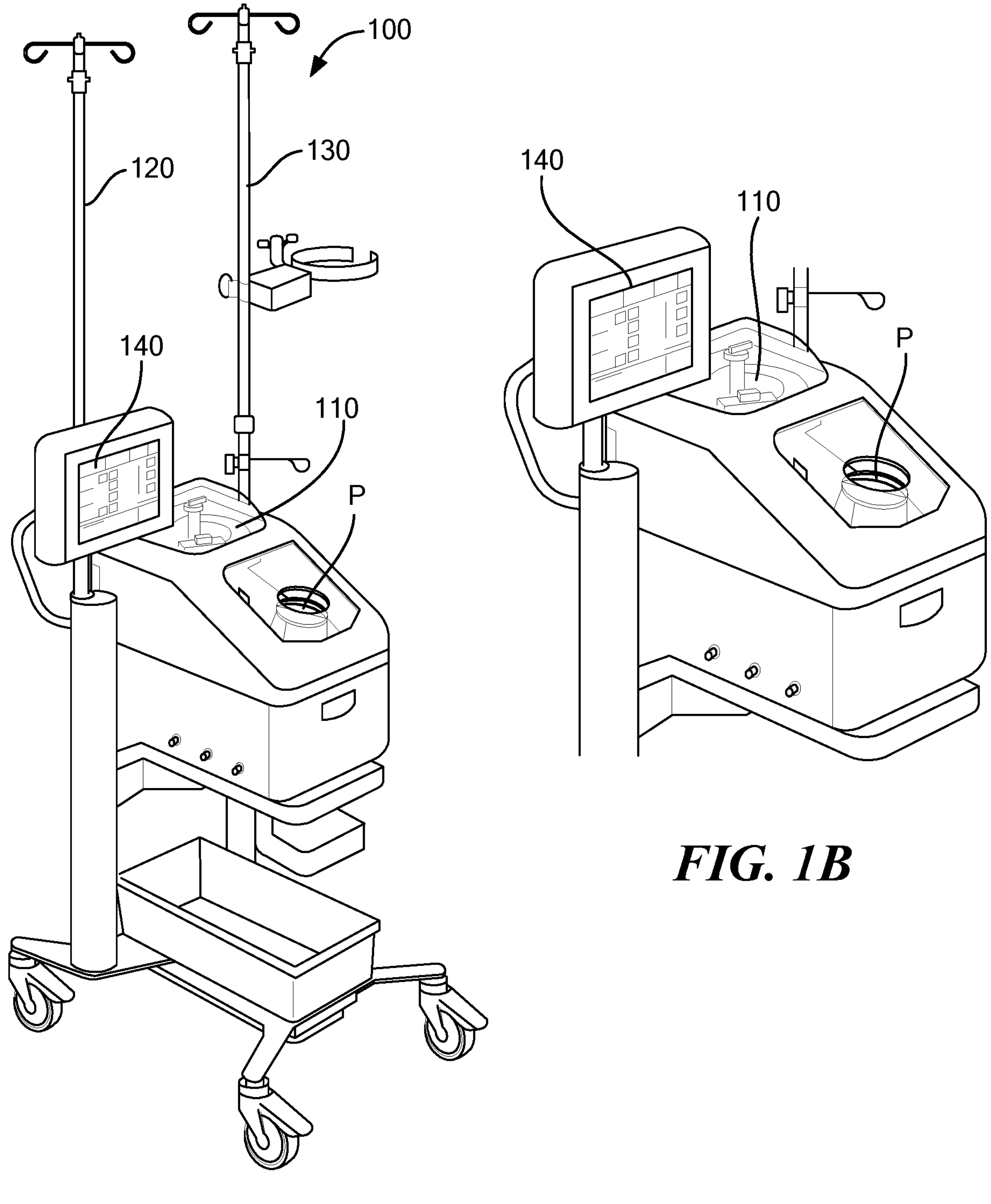
FIGS. 1A-1C schematically shows a processing device in accordance with embodiments of the present invention.
Figure 1C:
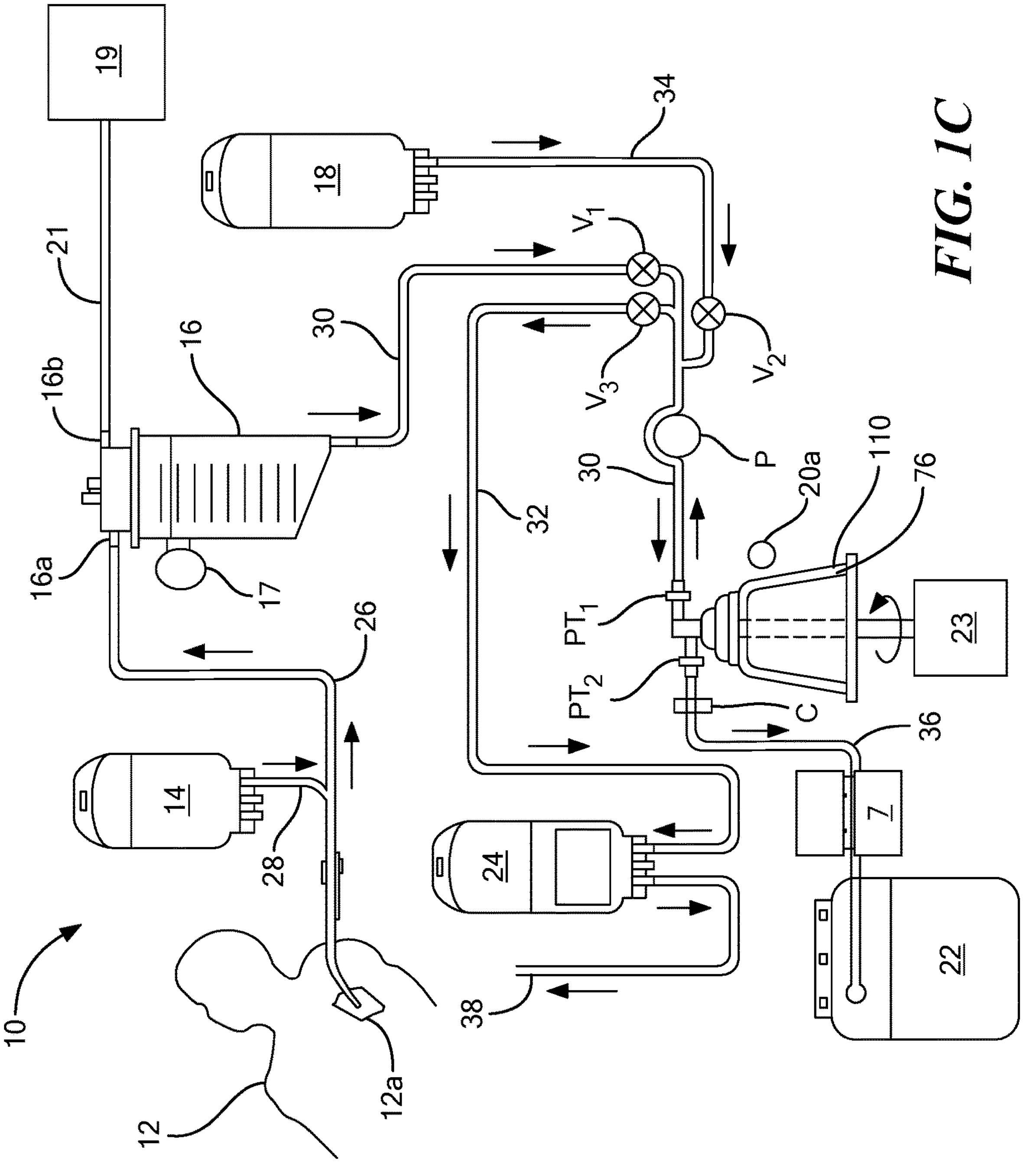

FIGS. 1A to 1C schematically show a blood/cell processing system 100 in accordance with some embodiments of the present invention. The system 100 includes a blood component separation device (e.g., a centrifuge bowl 110) that separates the whole blood into its individual components. For example, in some embodiments, anticoagulant may be added (from an anticoagulant bag hung from pole 120 connected to the processing system 100) to the blood/cells as it is transferred to the processing system 100. The blood is then introduced into the blood component separation device 110 (e.g. via a container/reservoir hung on pole 130 or directly from a patient), which separates the blood into its individual components (e.g., red blood cells, plasma, platelets, etc.). Once the blood is separated, the platelets and/or plasma may be transferred to a waste bag for disposal, and the processing system 100 may introduce a wash solution into the separation device to wash the red blood cells. After washing the red blood cells, the processing system 100 may return the red blood cells to the patient. The system 100 includes a display 140 (e.g., a touch screen display) that allows the user to interact with the system 100 before, during and after processing. Additionally, the system 100 may display information about the current procedure on the display 140 during processing.

For example, as shown in FIG. 1C, in a blood salvage application, the system 100 may include a suction line 26 for suctioning blood lost from a wound site 12*a* (or surgical site) of a patient 12. The suction line 26 is in fluid communication with a salvage reservoir 16 via a port 16*a* (e.g., an inlet port). The anticoagulant container is in fluid communication with the suction line 26 via a feed line 28. A vacuum source 19 is coupled to a port 16*b* (e.g., a vacuum port) of the reservoir 16 via a vacuum line 21. The vacuum source 19 provides a vacuum within the suction line 26 so that the suction line 26 can suction blood from the wound/surgical site 12*a* into the reservoir 16. As discussed in greater detail below, a reservoir level sensor 17 senses the level of fluid within the reservoir 16.

The reservoir 16 is in fluid communication with the centrifuge bowl 110 via line 30, valve $V_1$, and the inlet port $PT_1$. As noted above, the centrifuge 100 separates and washes salvaged blood received from the reservoir 16, and is rotated by a motor 23. An optical sensor 20*a* directed towards/aimed at the bowl 110 senses the level of hematocrit within the centrifuge bowl 110 by directing a beam of light into the centrifuge bowl 110 which is reflected back to the sensor 20*a*. If the beam of light is not reflected back to the sensor 20*a*, the centrifuge bowl 110 is considered full of red blood cells.

As also shown in FIG. 1C, a waste container 22 for collecting waste washed from the salvaged blood is fluidly coupled to the centrifuge bowl 110 via the outlet port $PT_2$ and an effluent line 36. The effluent line 36 passes through an optical line sensor 7 which senses the turbidity of the fluid flowing through the effluent line 36. The optical line sensor 7 may also control the speed of the pump P, the number of wash stages and the volume of wash solution employed for washing blood components. To facilitate the wash process, the system 100 may have a bag 18 containing a wash solution. The wash fluid container 18 may be fluidly coupled to the centrifuge bowl 110 via a wash line 34, the valve $V_2$, the line 30, and the inlet port $PT_1$.

To collect the final/washed blood components (e.g., red blood cells), the system 100 also includes a collection bag 24 that, in turn, is fluidly connected to the centrifuge bowl 110 via the inlet port $PT_1$, line 30, valve $V_3$ and line 32. In some embodiments, the system 100 has a line 38 connected to an outlet of the collection bag 24. This line 38 allows fluid collected in the collection bag 24 to be transferred into a secondary reinfusion bag (not shown) in which air is removed for pressurized reinfusion into the patient 12 via a phlebotomy needle. Alternatively, the fluid collected in the collection bag 24 may be gravity fed into the patient 12 via a phlebotomy needle and line 38. Valves $V_1$, $V_2$ and $V_3$ are remotely operated to control the directional flow of fluids pumped by the pump P within the apparatus 100. The pump P may be a peristaltic pump for pumping fluids into and out of centrifuge bowl 110. Optionally, a clamp C can be included for clamping effluent line 36.

Generally, during operation, blood from the wound 12*a* (or surgical site) is suctioned from the patient 12 via a suction line 26. The suctioned blood is anticoagulated with anticoagulant dripping from the anticoagulant bag 14 via the feed line 28 and stored in reservoir 16. As noted above, the reservoir 16 may include a level sensor 17 that senses the level of salvaged blood within reservoir 16. Once a predetermined amount of salvaged blood is stored/has been collected within the reservoir 16, the level sensor 17 (or a controller) activates the pump P which begins what is to be referred to as the fill mode by pumping salvaged blood into the centrifuge bowl 110 from the reservoir 16 via line 30, valve $V_1$, and inlet port $PT_1$, with valve $V_1$ open and valves $V_2$ and $V_3$ closed. The rate of the pump P is controlled by the optical line sensor 7 and/or the controller.

The blood enters the separation chamber 76 of the centrifuge bowl 110 and, as the centrifuge bowl 110 is filled with blood, the centrifuge bowl 110 is rotated by the motor 23, separating the blood within separation chamber 76 into different fractions in accordance with the component densities. When in the bowl 110, centrifugal forces separate the blood into higher density components (mainly red blood cells (RBCs)), intermediate density components (mainly white blood cells and platelets), and lower density components (mainly plasma). The RBCs are forced to the outer wall of the centrifuge bowl 110 while the plasma remains nearer to the core of the centrifuge bowl 110. A "buffy coat" is formed between the plasma and the RBCs. The "buffy coat" is made up of an inner layer of platelets and an outer layer of white blood cells (WBCs).

As the bowl 110 is filled with blood, the RBC layer moves in radially, resulting in its boundary rising upwards. The optical sensor 20*a* is positioned relative to the centrifuge bowl 110 such that when the bowl 110 is filled (e.g., to approximately 50% hematocrit), the upwardly rising RBC layer scatters the beam of light generated by the optical sensor 20*a*. As a result, the optical sensor 20*a* does not receive a reflected beam of light and the optical sensor 20*a* determines that the centrifuge bowl 110 is full. Once the optical sensor 20*a* determines that the bowl 110 is full (e.g., to approximately 50% hematocrit), the pump P stops pumping and the filling of the centrifuge bowl 110 is terminated. As noted above, once the blood is separated, the platelets and/or plasma may be transferred to a waste bag for disposal, and the processing system 100 may introduce a wash solution into the separation device to wash the red blood cells. After washing the red blood cells, the processing system 100 may return the red blood cells to the patient.

It should be noted that traditional processing systems are "state machines" with pre-defined protocols that define the operation of the system. For example, the system will stay in the current (and pre-defined) state until a decision point, then the protocol will move the system to the next state until a subsequent decision point is reached. In such systems, the user has very little flexibility as to the state or the decision points (e.g., the user cannot alter the protocol significantly). However in many applications, particularly in academic and cell therapy applications, it may be useful for the user to either alter a protocol or even create a new protocol altogether. To that end, some embodiments of the present invention have a "flex mode" that allows the user to define both the state (selections of critical parameters) and the decision points.

As discussed in greater detail below, the flex mode allows the user to create custom protocols and settings groups (e.g., wash volume, fill speed, empty speed etc.) for the locked state behavior FILL, WASH, EMPTY, for example. The user may also define the critical parameters for the protocol and each of the states. Examples of critical parameters include, but are not limited to pump speed, valve position, and centrifuge speed. Examples of decision points include simple points such as button presses, to more complex system feedback such as effluent cleanliness level reached, Bowl Optics RBC detection slope value reached, target volume reached, time at state, centrifuge speed reached, etc.

Additionally, in some embodiments, the system 100 may allow the user to select and customize additional options to further optimize the protocol and customize the protocol to the specific application. For example, the user may select the messages to be shown on the display 140. These messages may include the types of warning messages, process information (e.g., flow rates, pressures, volumes, the present processing stage, etc.) and/or instructions to the user (e.g., to connect various components, perform a manual task, etc.). Additionally or alternatively, the user may input volumes for pre-determined states such as the fill volume (or other volumes that determine the beginning or end of a process step) that may change from procedure to procedure. As discussed in greater detail below, once the protocol has been created, the user may save the custom protocol for later use (e.g., in a data storage device/database) and may password protect each saved protocol to ensure that it is not inadvertently edited. The workflow/protocol may be created either through visual drag and drop of pre-defined states on the touchscreen or through a menu with add/delete buttons.

Figure 2:
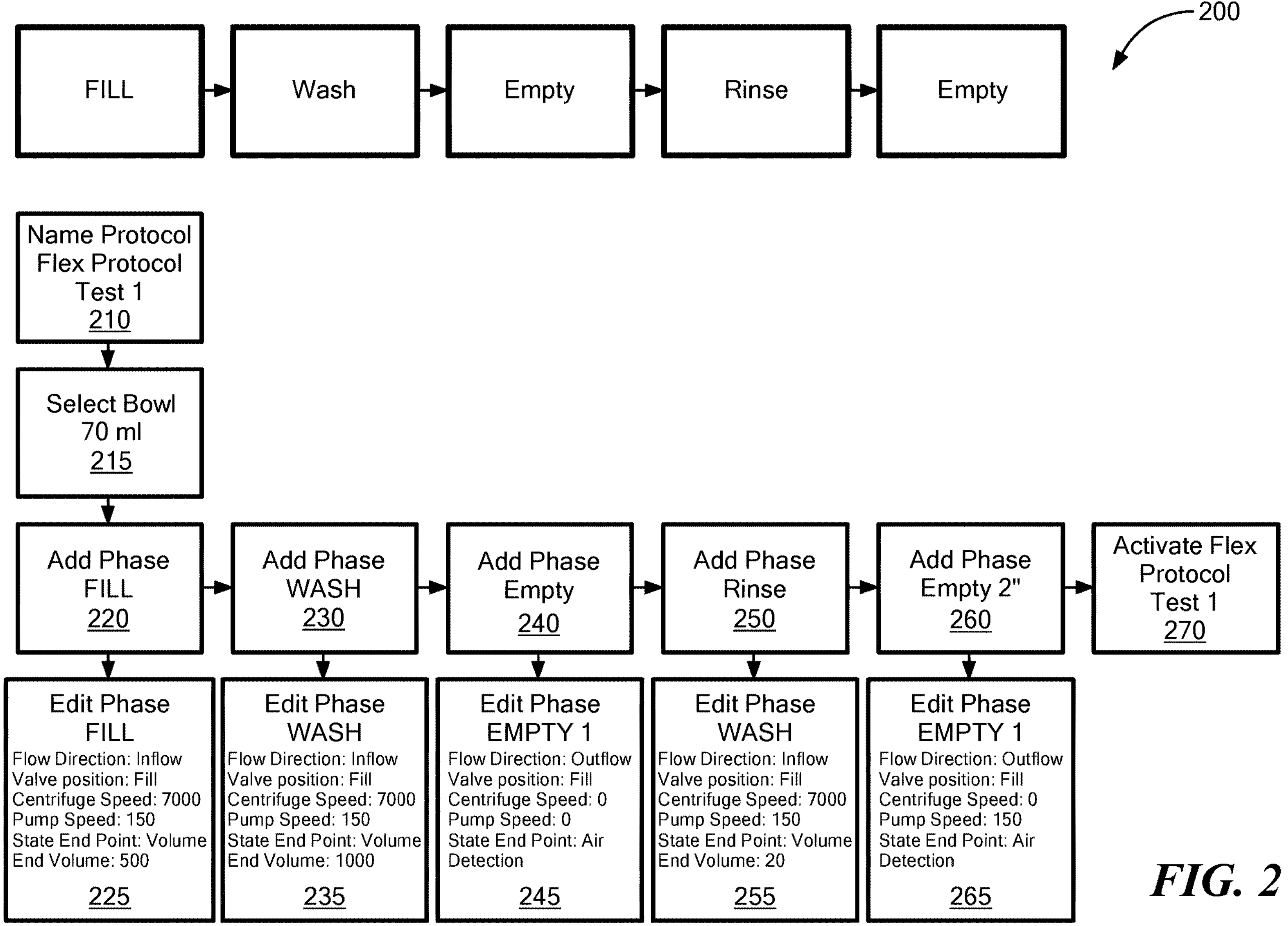
FIG. 2 is a flowchart depicting a method of creating a custom protocol in accordance with embodiments of the present invention FIGS. 3A-3J schematically show screenshots depicting the user interface at various steps of the method shown in FIG. 2, in accordance with embodiments of the present invention.

FIG. 2 is a flowchart depicting an exemplary process for creating a custom protocol in accordance with embodiments of the present invention. FIGS. 3A to 3J show exemplary screenshots from the display 140 as the user proceeds through the protocol creation process. It should be noted (and as discussed in greater detail below) that, although FIG. 2 shows the creation of a protocol with a FILL-WASH-EMPTY-RINSE-EMPTY workflow other protocols/workflows can be created. Generally, the protocol created in FIG. 2 is similar to a standard 70 ml bowl default except the fill phase automatically runs to a set end volume instead of an air detect, a small 20 ml rinse step is added after the first empty, and a second empty is added after the rinse. However, other protocols that vary significantly from that shown in FIG. 2 may be created.

Figure 3A:
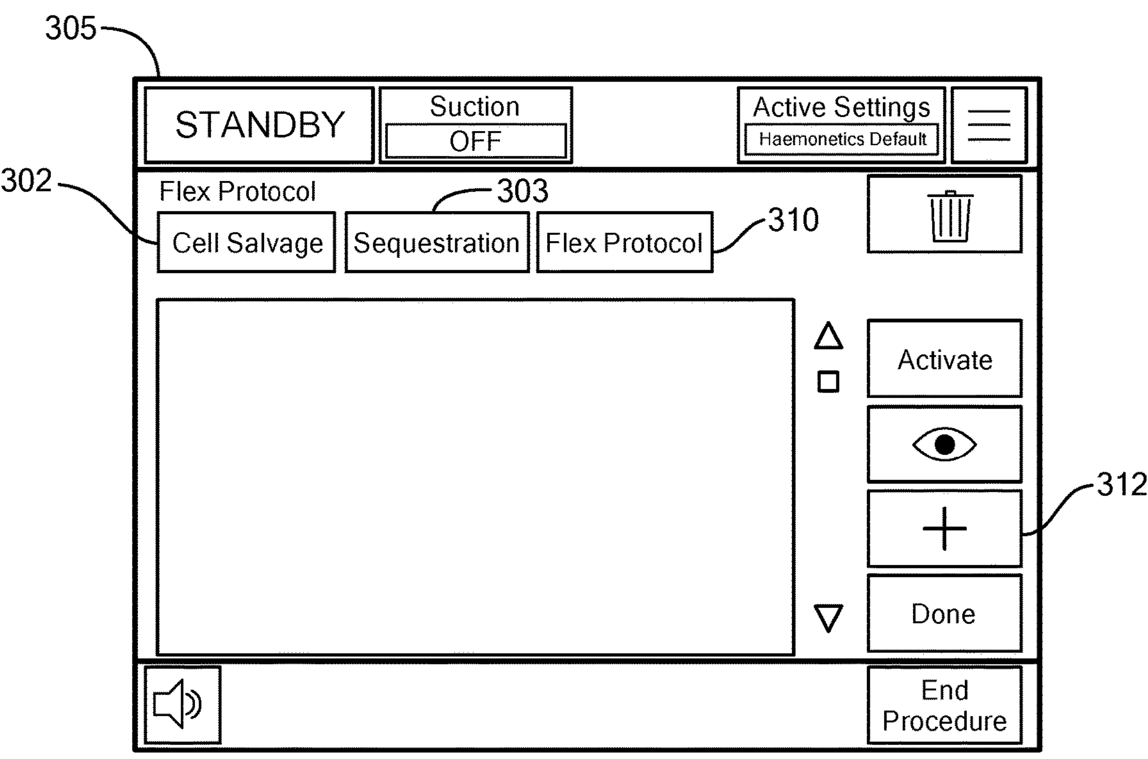
Figure 3B:
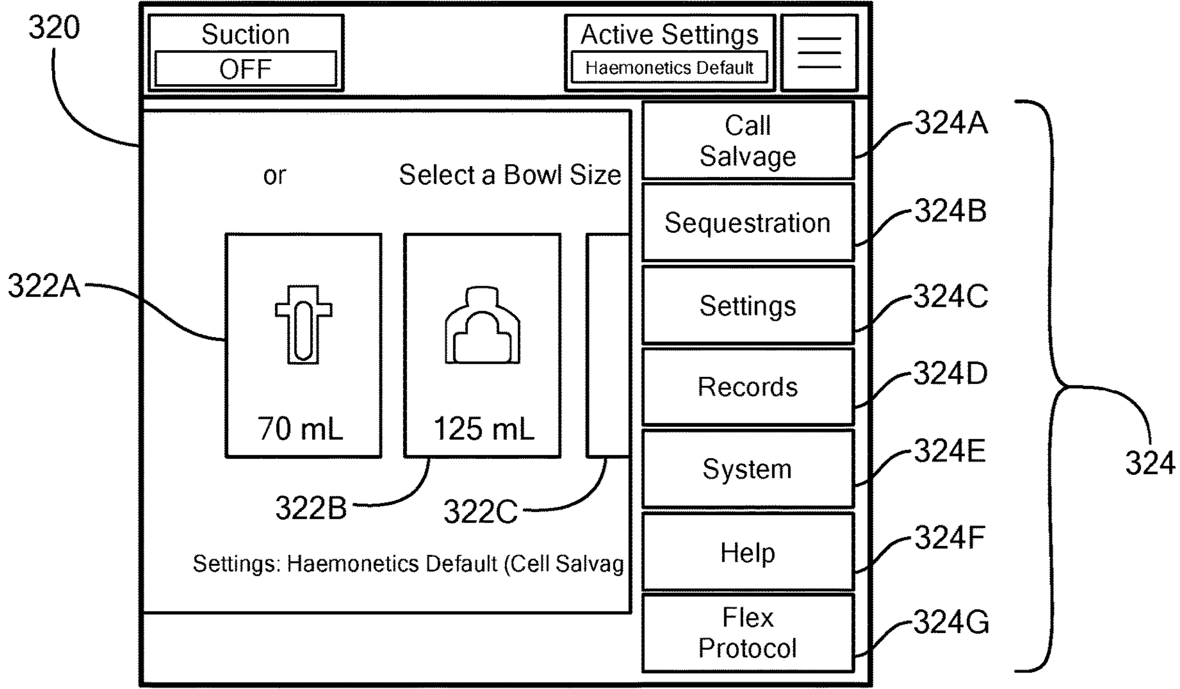

Upon start-up of the system 100, the display/interface 140 may show a "main screen" 305 with a number of options/buttons for the user to select such as "cell salvage" 302 and/or "sequestration" 303 (FIG. 3A). As discussed in greater detail below, this main screen 305 may also include a listing of all previously created custom algorithms/protocols. The user may select "flex protocol" 310 on the display 140 to begin creating a customized protocol (FIG. 3A). To allow the user to name the custom protocol (Step 210), the display/touchscreen 140 may provide the user with a keyboard on the screen and the user may type in the name of the protocol using the touch screen 140. Alternatively, the system 100 may include a separate keyboard that the user may use to type in the name of the protocol. Once the name has been entered, the system 100 will display a "bowl selection screen" 320. Using this screen, the user can select the type and size of bowl 322A/B/C that they wish to use for this custom protocol (Step 215). For example, the user may select a 70 mL bowl 322A, a 125 mL bowl 322B, or a 225 mL bowl 322C.

Figure 3C:
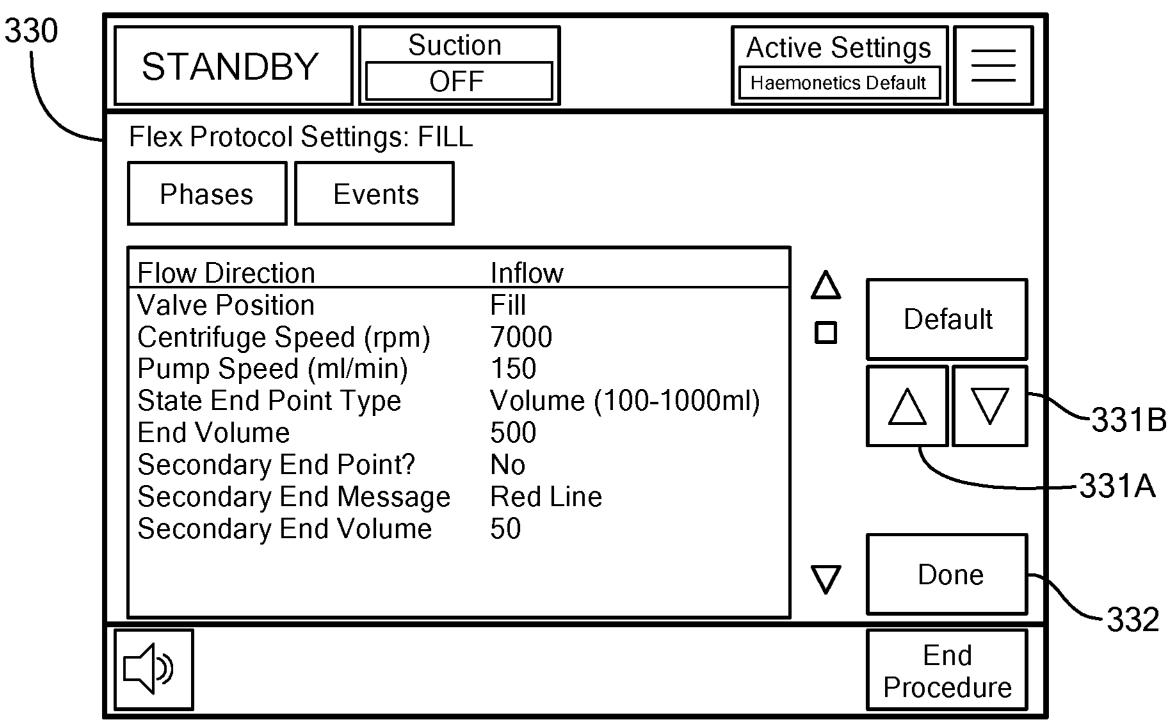

After the user has selected the desired bowl, the system 100 may return to the main screen 305 (FIG. 3A). Alternatively the user can manually return to the main screen using the navigation buttons 324 located on the side of the bowl selection screen 320. For example, the navigation buttons may include a "cell salvage" button 324A, a "sequestration" button 324B, a "settings" button 324C, a "records" button 324D, a "system" button 324E, a "help" button 324F, and a "flex protocol" button 324G. The user may press the "flex protocol" button 324 G to return to the main flex protocol screen 305. At the main screen 305, the user may add a phase by pressing the "+" button 312 and selecting a phase, for example, a fill phase (Step 220). The system will then bring up a "build fill phase" screen 330 that allows the user to customize the settings of the fill phase. For example, the user may use the up and down buttons 331A/B to scroll through the various details of the fill phase and customize the settings for each (Step 225)(FIG. 3C). For example, the user may set the flow direction to inflow, the valve position to fill, the centrifuge speed to 7000, the pump speed to 150, set the end point state to volume, and the end volume to 500. After the desired settings have been entered, the user may press done 332 to complete the fill phase. At any point, if the user wishes to use default settings, the user may simply press the default button 333 and the system 100 will automatically set each of the settings to default parameters.

Figure 3D:
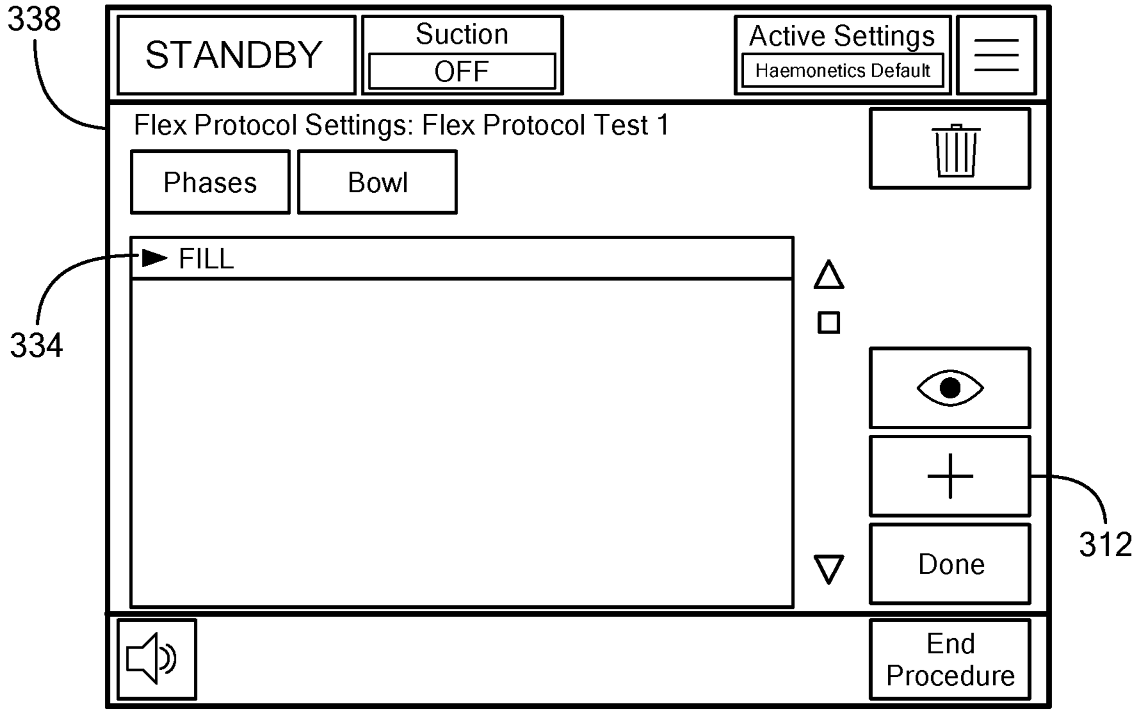
Figure 3E:
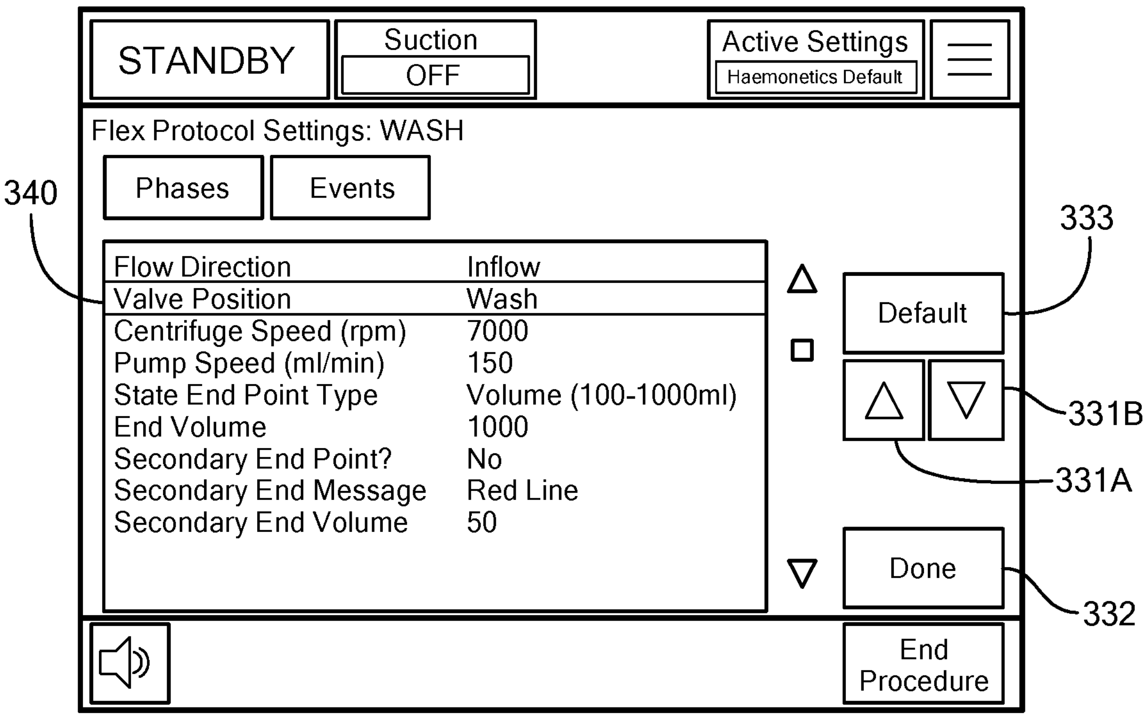

The system 100 will then move to a flex protocol page 338, FIG. 3D, that shows that the fill phase 334 has been built and added to the protocol. To add the next phase, in this instance a wash phase (Step 230), the user may once again press the add button 312 and select a wash phase. In a manner similar to the fill phase, the user may use the up and down buttons 331A/B on the wash phase screen 340 to navigate between the various details/aspects of the wash phase to edit/customize the wash phase of the protocol (Step 235). For example, as shown in FIG. 3E, the user may set the set the flow direction to inflow, the valve position to wash, the centrifuge speed to 7000, the pump speed to 150 and set the end point state to volume and the end volume to 1000. Once the user has completed building the wash phase, they may press the done button 332 to complete the wash phase and add the customized wash phase to the protocol.

Figure 3F:
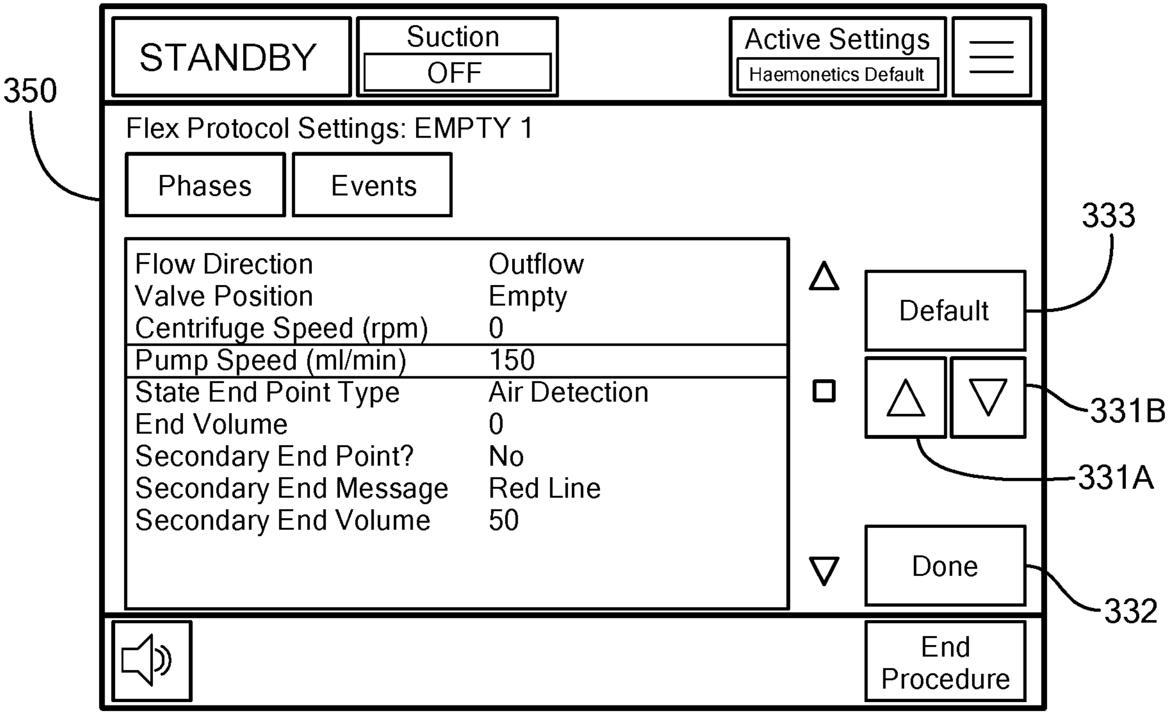
Figure 3G:
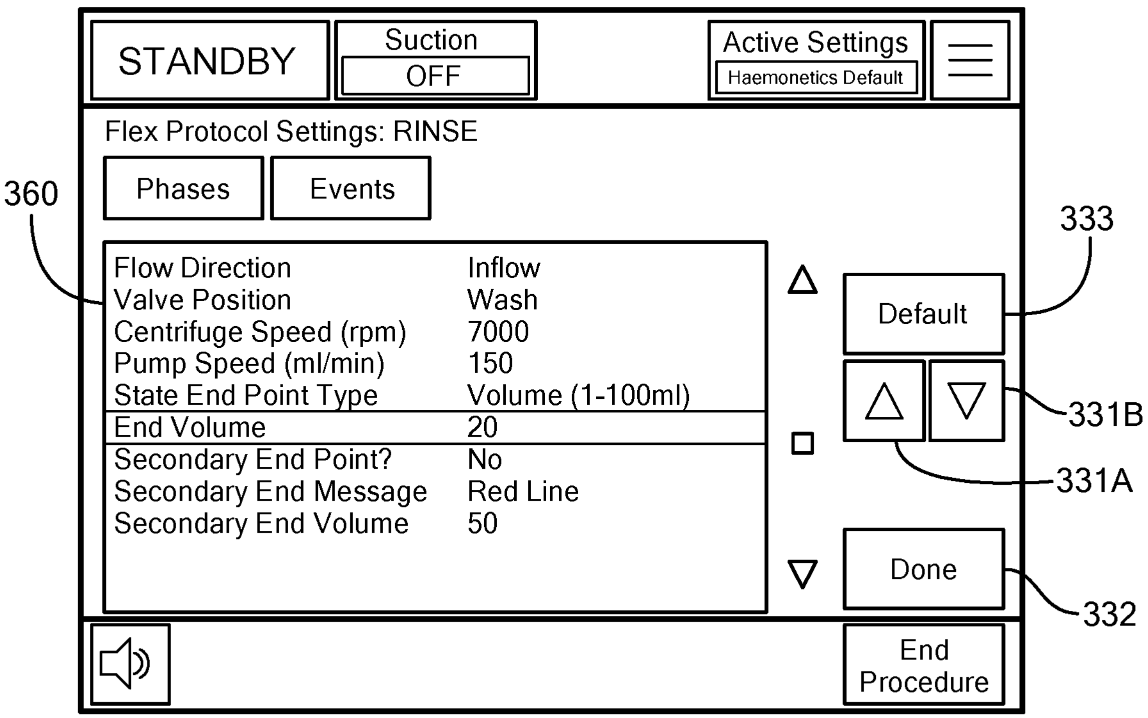
Figure 3H:
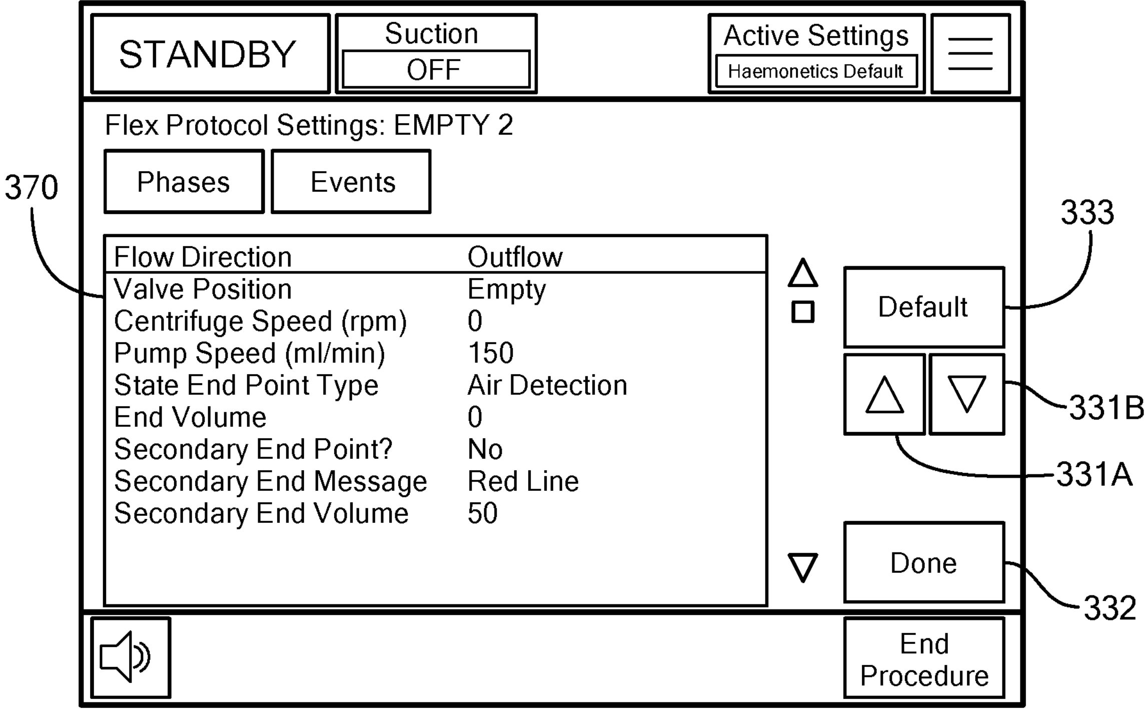
Figure 3I:
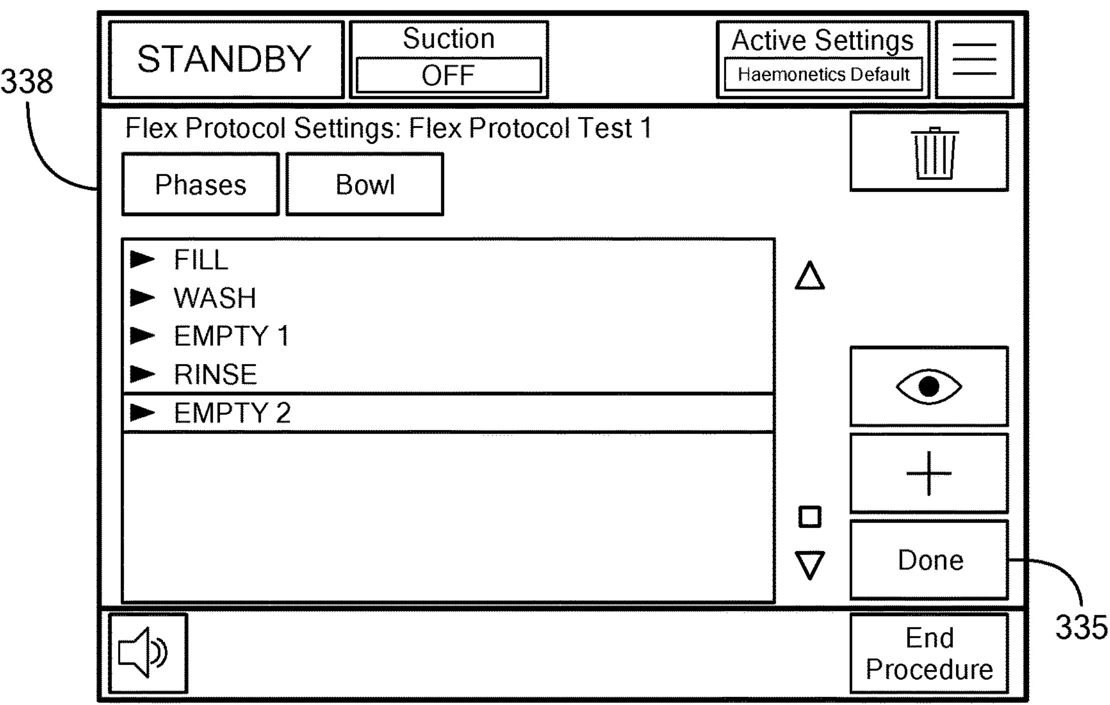
Figure 3J:
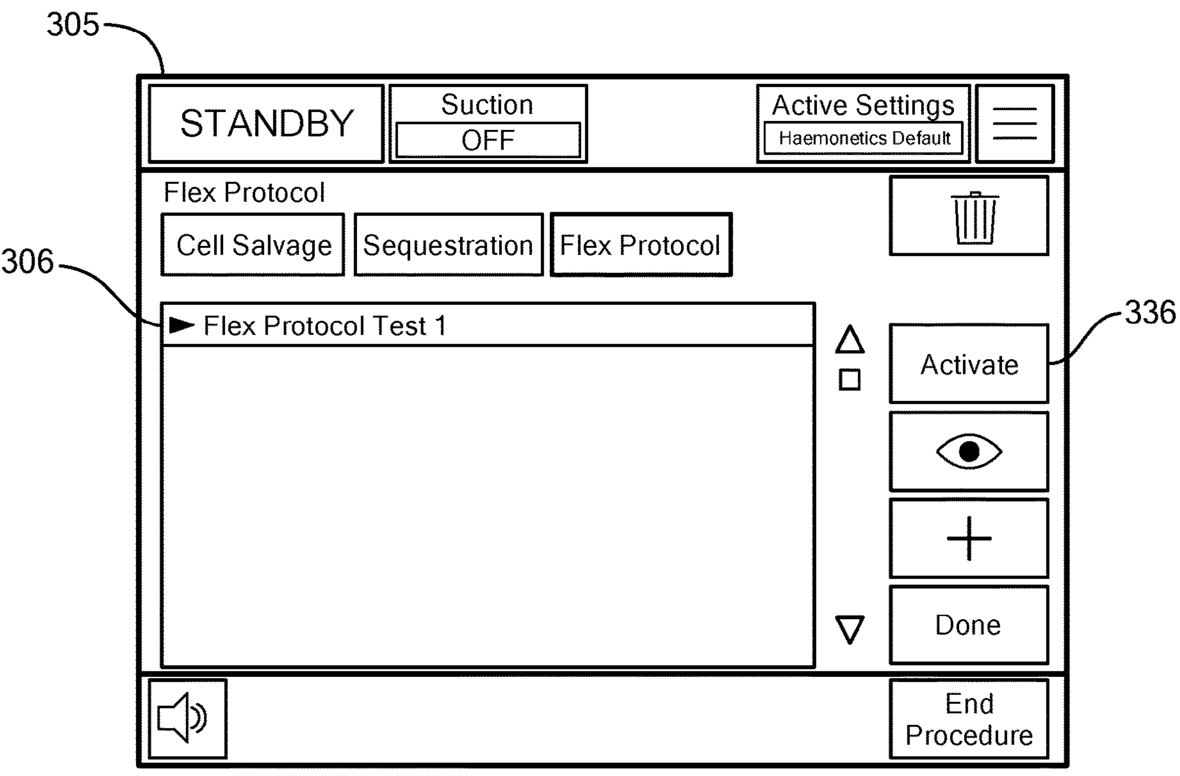

The user may continue the process to add and edit any additional phases. For example, the user may add and edit an empty phase (Steps 240 and 245), a rinse phase (Steps 250 and 255) and a second empty phase (Steps 260 and 265). As shown in FIGS. 3F to 3H and in a manner similar to that described above (e.g., using the up/down buttons 331A/B etc.), the user may customize the various parameters of each of the empty phases and rinse phases on their respective screens 350, 360, 370 to customize the overall processing protocol. Once the user has added and edited each the desired phases (e.g., the fill, wash, empty, rinse phases) each of the phases will be displayed on the flex protocol page 338 (FIG. 3I), and the user may press the done button 335 to complete/finalize the protocol. At this point, the system 100 will create the algorithms necessary for the system 100 to carry out the protocol when the user is ready. For example, the system 100 may include a processor that creates the protocol based on the selected phases and the edited parameters within each selected phase. Once the system 100 has created the algorithm/protocol, the system 100 may store the algorithm/protocol (e.g., within a database and/or data storage device) so that it can be used at a later time and may add the protocol to the available protocol list 306 on the main screen 305 (FIG. 3J). To continue with performing the created protocol (e.g., to perform the protocol using the blood component separation device), the user may return to the main screen 305 and select the desired protocol from the list (FIG. 3J) and press the activate button 336 (Step 270). The system will then proceed to carry out the protocol.

Figure 4:
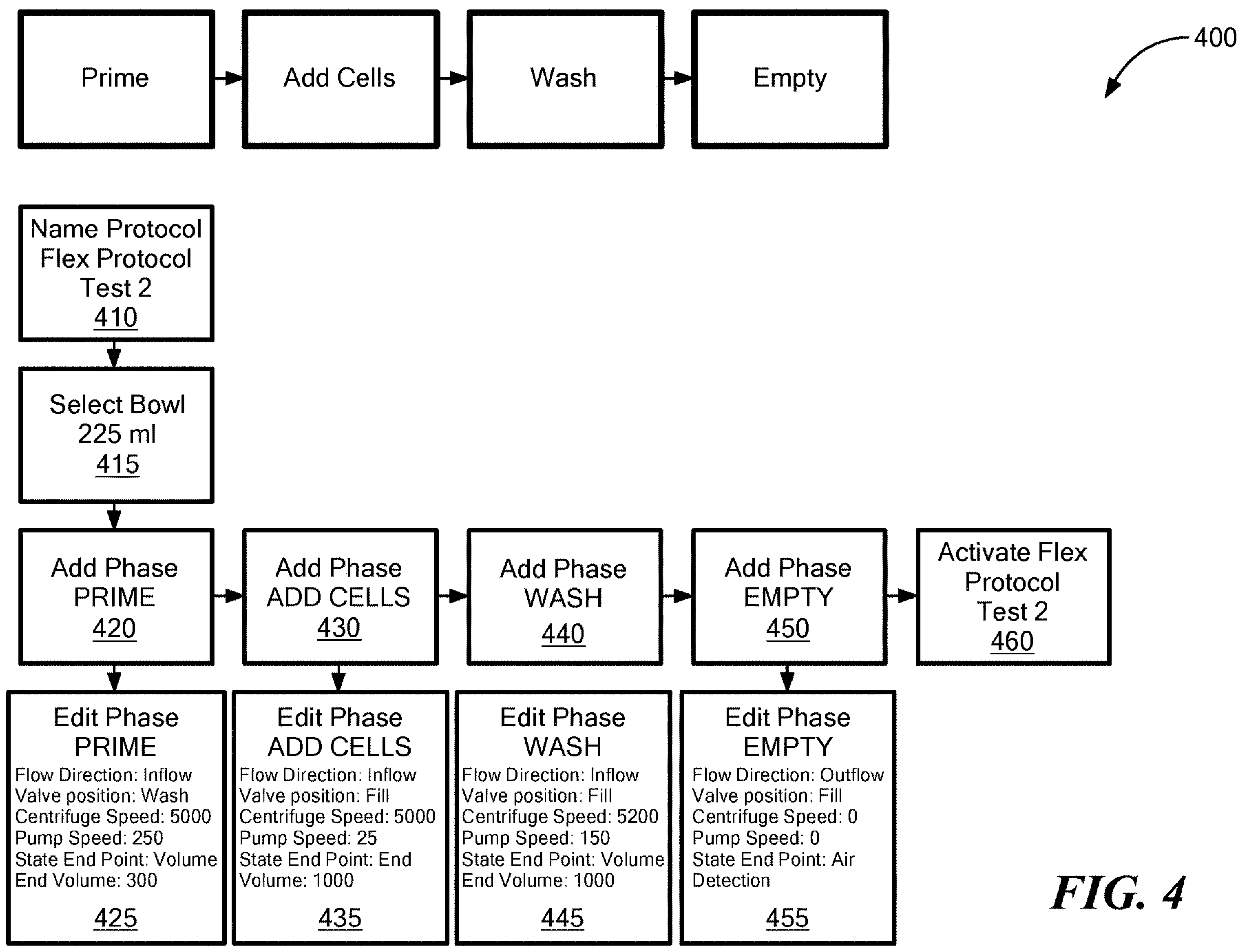
FIG. 4 is a flowchart depicting a method of creating a second custom protocol in accordance with embodiments of the present invention.

It should be noted that although the embodiment described above creates a protocol that includes a fill phase (e.g., a phase in which the bowl 110 is filled with blood/blood components), a wash phase (e.g., in which wash solution is introduced into the bowl to wash the red blood cells), an empty phase (e.g., in which a portion of the contents of the bowl 110 are emptied), a rinse phase (e.g., in which a small volume of solution is introduced into the bowl 110 to rinse the contents) and a second empty phase (e.g., in which the bowl 110 is emptied), other embodiments can create different protocols with different phases. For example, FIG. 4 is a flowchart depicting an exemplary process for creating a different custom protocol in accordance with additional embodiments of the present invention. FIGS. 5A to 5F show exemplary screenshots from the display 140 as the user proceeds through the protocol creation process. It should be noted (and as discussed in greater detail below) that FIG. 4 shows the creation of a protocol with a PRIME-ADD CELLS-WASH-EMPTY workflow. This protocol uses a 225 mL bowl and first primes the bowl (e.g., with anticoagulant or wash solution) from the wash line 34. The protocol subsequently fills the bowl with a pre-determined & flexible volume set by the user during the procedure based on the variable volume of cells (in ml). The system 100 then performs a wash step and a standard empty step/phase.

To create this protocol, in a manner similar to that described above and upon system start-up, the user may select the flex protocol option to begin creating the custom protocol. The user may then name the protocol (e.g., "Flex Protocol Test 2" in FIG. 4) (Step 410) and select the desired bowl size (e.g., 225 mL)(Step 415). Once the bowl size has been selected, the user may then press the add button 312 to add a custom prime phase (Step 420). It should be noted that, because this is not a standard phase, the user can name the phase (e.g., "Prime" in FIG. 5A) using the keyboard 505 and then edit/customize each the parameters as needed (Step 425) on the prime phase screen 510. For example, the user may set the flow direction to inflow, the valve position to wash, the centrifuge speed to 5000, the pump speed to 250, and the endpoint to a volume of 300 mL. After editing the prime phase, the user may press the done button 335 to add the phase to the protocol.

Figure 5A:
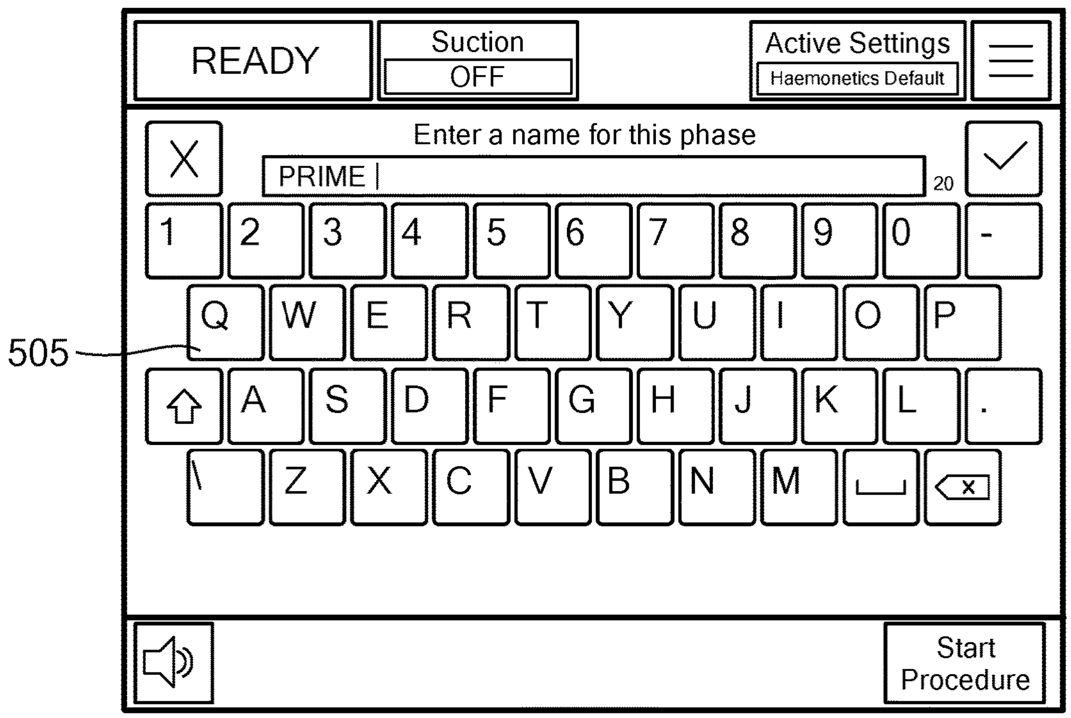
FIGS. 5A-5F schematically show screenshots depicting the user interface at various steps of the method shown in FIG. 4, in accordance with embodiments of the present invention.
Figure 5B:
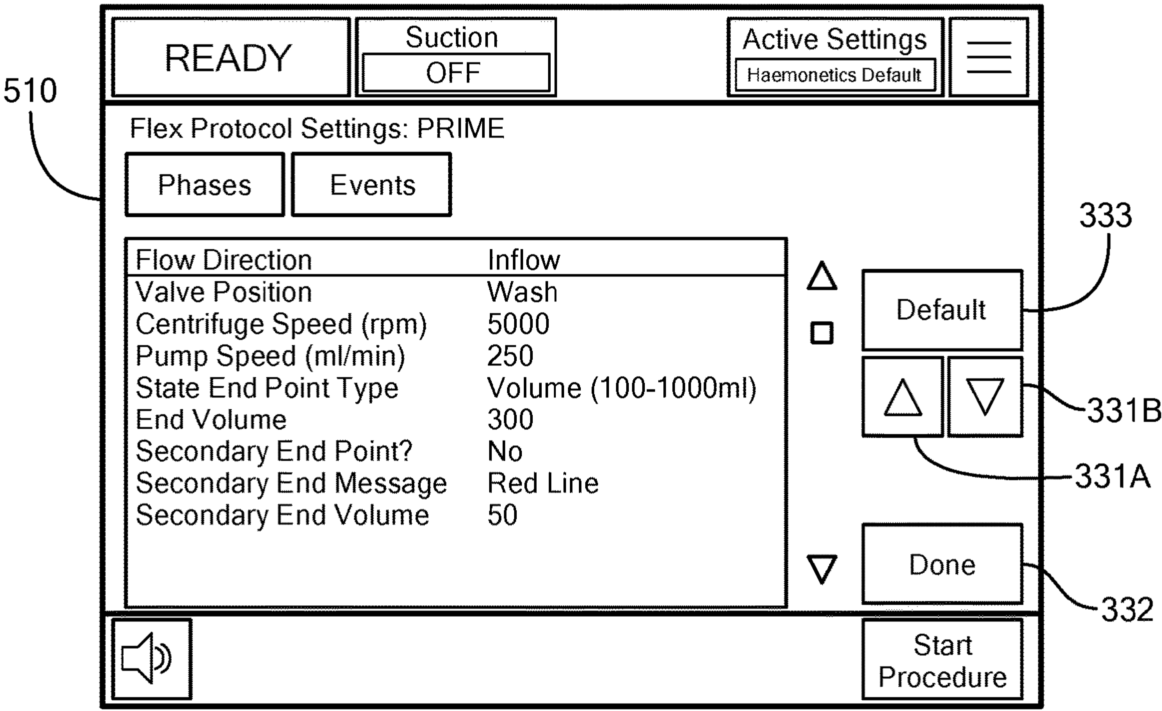
Figure 5C:
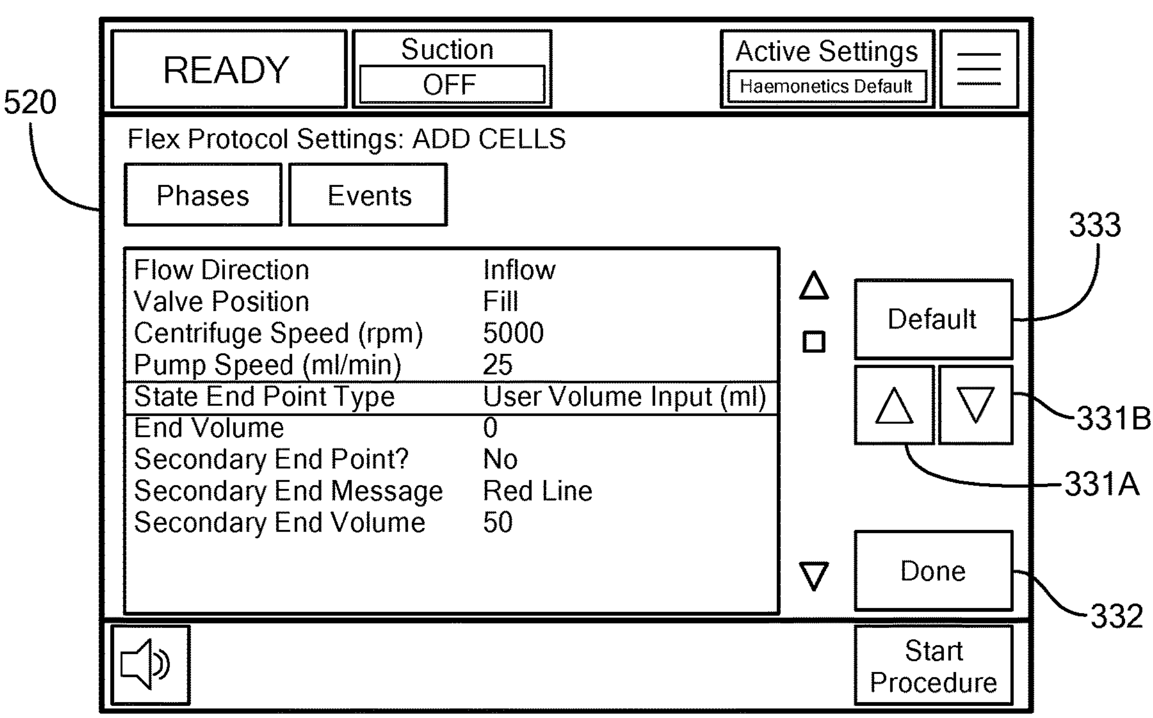
Figure 5D:
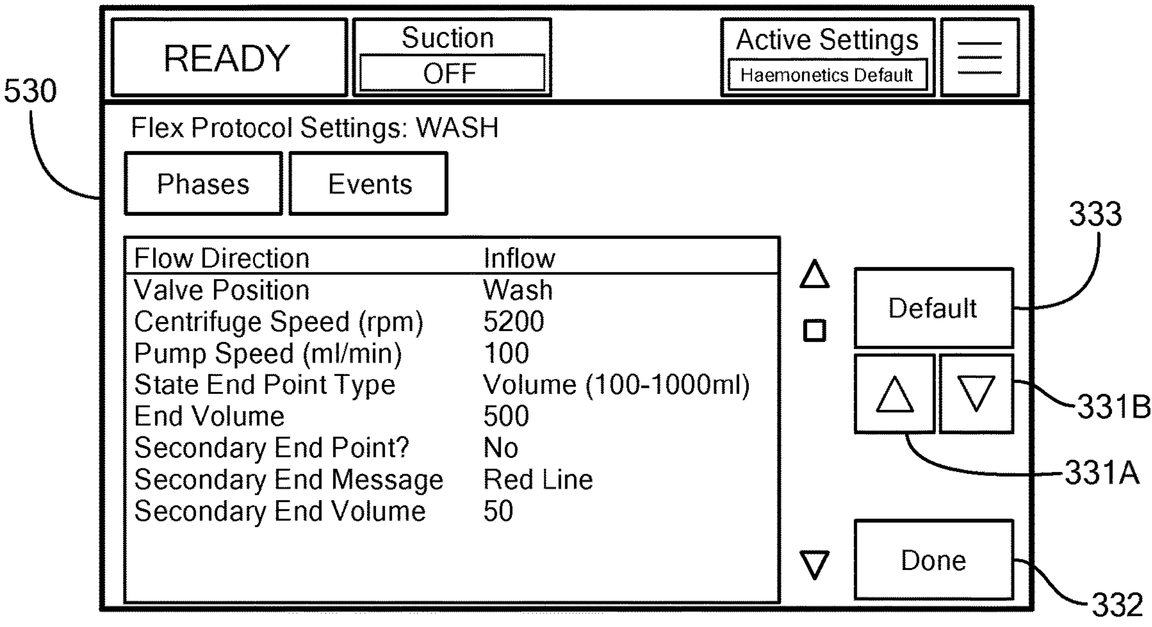
Figure 5E:
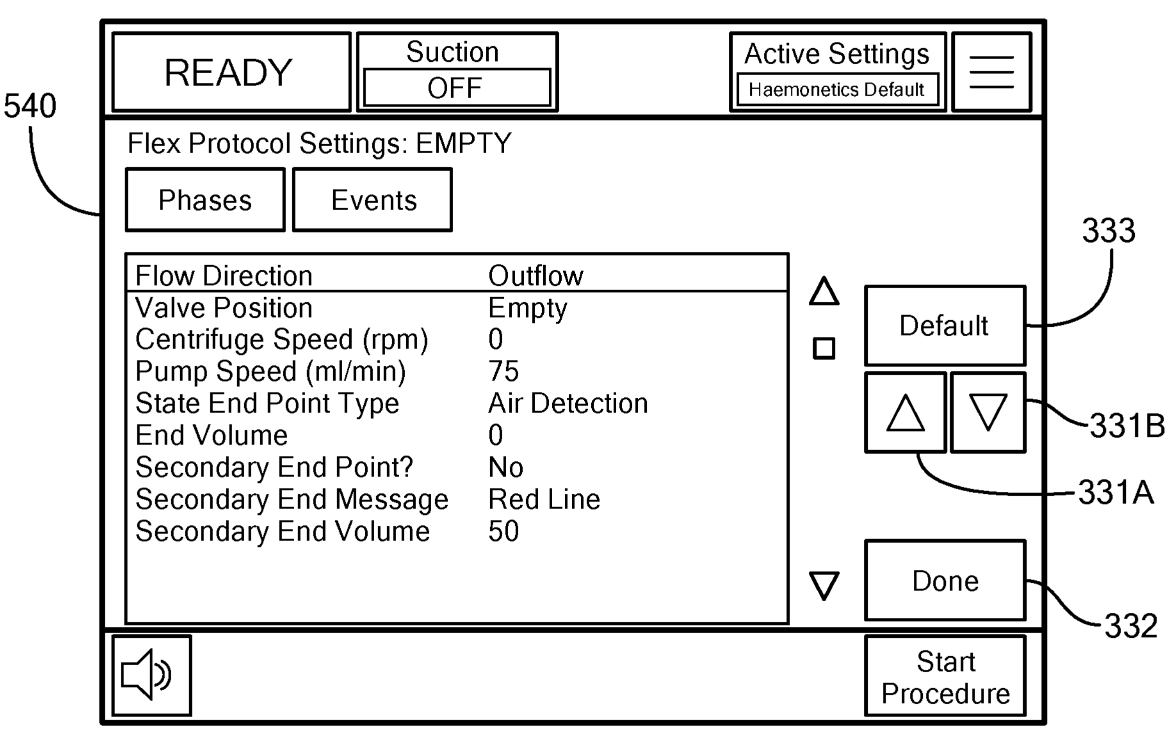
Figure 5F:
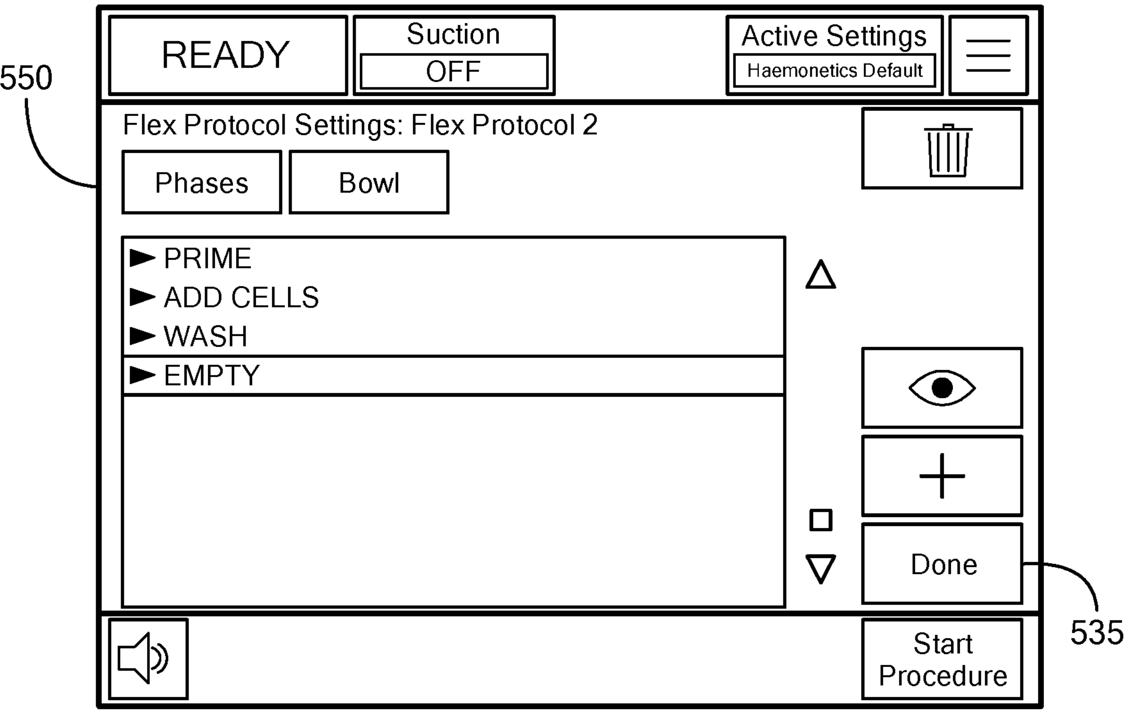
Figure 6:
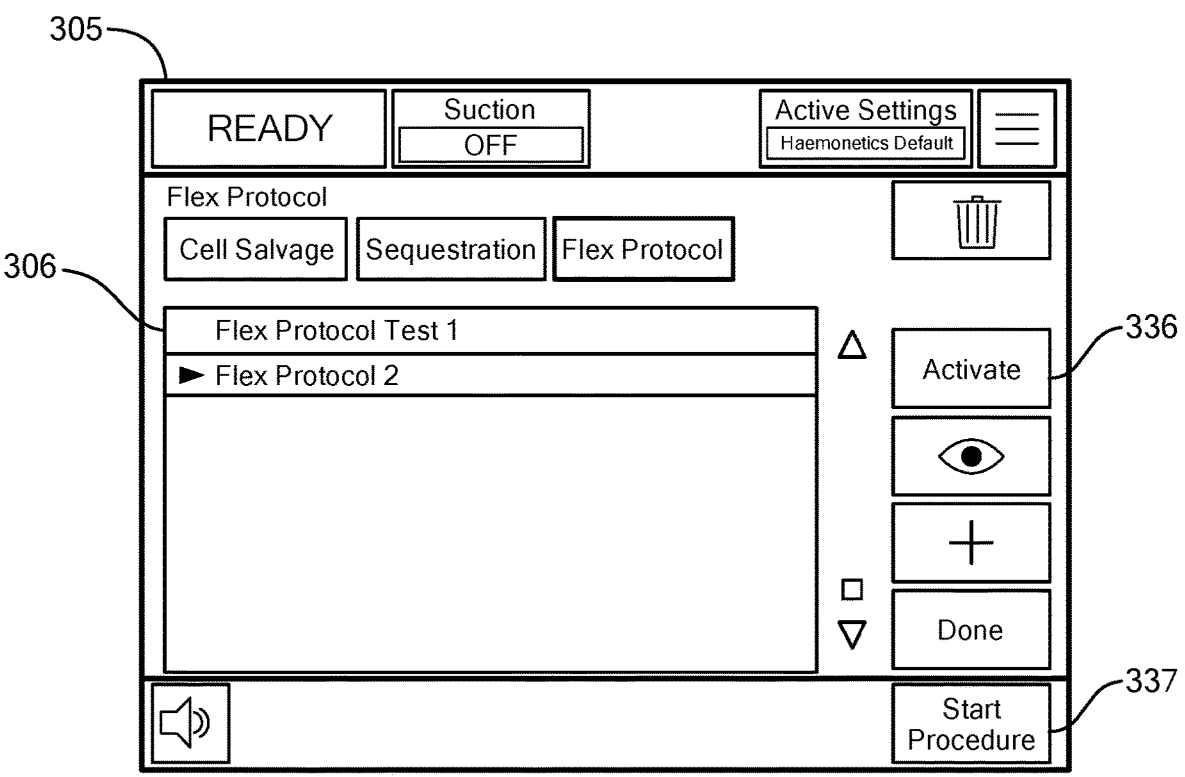
FIG. 6 schematically shows a screenshot depicting the protocols created as shown in FIGS. 2 and 4, in accordance with embodiments of the present invention.

The user may then continue in a similar manner adding and editing the additional phases for the protocol. To create the protocol shown in FIG. 4, the user may add and edit an "add cells" phase (Steps 430 and 435; FIG. 5C) on the add cells screen 520, add and edit a wash phase (Steps 440 and 445; FIG. 5D) on the wash phase screen 530, and add and edit the empty phase (Steps 450 and 455; Step 5E) on the empty phase screen 540. It should be noted that, although FIGS. 4 and 5A-5E show specific parameters selected, embodiments of the present invention allow the user to customize each of the phases and, therefore, the user can change any of the parameters shown in the figures. To finalize and create the protocol (and the algorithms necessary for the system 100 to carry out the protocol), the user may select done 335 on the protocol screen 550 which, in turn, adds the newly created protocol (e.g., Flex Protocol 2) to the list of available protocols on the startup/main screen 305 (FIG. 6).

When the user is ready to start a blood or cell processing procedure, the user may select the desired protocol from the list (e.g., "Flex Protocol 2") and press the activate button 336 (Step 460). This will active the selected protocol and load the parameters of the protocol. Once the protocol is loaded and the user has set up the system 100/device, the user may then press the "start procedure" button 337 to begin the procedure.

It is important to note that by allowing users to customize and create any number of protocols, embodiments of the present invention allow the system 100 to be used in academic settings. Additionally, embodiments of the present invention may be used in applications where a workflow other than the standard Fill Wash Empty phases are used, and may provide a more targeted solution for cell therapy customers/applications. With respect to cell therapy, GMP processes typically utilize a custom workflow that requires execution of a manual set of steps. This is prone to user error and has inherent variability of the end points of each phase. Various embodiments of the present invention allow a user to develop a customizable and reproducible protocol that provides the level of automation necessary to reduce variability in the process. Additionally, the system 100 may maintain procedure records that provide traceability and objective evidence of procedure date, time, processed volumes, product volume, etc.

In addition to the cell salvage procedures discussed above, some embodiments may allow the customization of sequestration algorithms available on some processing systems (e.g., e.g., the Cell Saver® Elite® and/or Cell Saver® 5+ systems sold by Haemonetics Corporation of Braintree, MA), which distributes the effluent into two bags (e.g., Platelet Rich Plasma, and Platelet Poor Plasma). The adjustment of the algorithm could be helpful to realize automation and standardization across ficoll separation programs using the sequestration algorithm. Various embodiments of the flex protocol may be utilized across academic applications for building design of experiments in a controlled manner, reducing variability inherent to manually running device.

It should be noted that it is important to ensure the safety of the patient/donor and also the system. Current cell processing/salvage systems include monitoring systems that monitor various aspects of the process such as centrifuge speed, manifold pressure/vacuum detection, fluid detection expectation windows for bowl types, volume counting/monitoring through the air detector, effluent air/plasma fluid detection expectations, bowl optics air plasma fluid detection systems, fluid spill detection in the centrifuge, and the cover lock. Embodiments of the present invention may utilize similar/the same state behavior as the validated cell salvage mode. Therefore, the same guardrails exist for performance safeguarding. For instance, pumping bowl contents to the empty destination with the empty line clamped manually by the operator would yield an excessive pressure in the blue line warning. Similarly, if the protocol causes the system 100 to pump fluid to the bowl 110 from wash line with a line clamped, a saline empty message would occur.

Some embodiments of the present invention may also validate a created protocol, for example, to ensure that the protocol will work as intended and ensure that there are no safety issues. In such embodiments, the system 100 may include a custom validation program that validates the created protocol using a simulation mode or through a standard regression type verification and validation ("V&V") test. If the system 100 determines that the created protocol would be problematic (e.g., would be dangerous to the system 100 or patient, or create an error message), the system 110 may alert the user so that the user may change the protocol and/or parameters as necessary prior to carrying out the protocol.

Although the above embodiments allow the user to fully customize the protocol, some embodiments may include pre-set application based modes. For example, the system 100 may include the option to have modes that toggle/adjust the performance of entire algorithm based on the selected mode. For instance, some embodiments may have a high quality mode, a default mode, and/or an expedited mode. These modes may vary the pump speeds accordingly to achieve the desired outcome (e.g., to receive a higher quality product, to speed up procedure time, etc.). The high quality mode may operate the pump speed at a very slow speed (in accordance with bowl size). For instance, under the high quality mode using a 70 ml bowl, the system operates the pump at speeds as low as 25 ml/min. Conversely, for the expedited mode, the system may operate the pump at speeds as high as 200 ml/min with the 70 ml bowl. For the 225 ml bowl, the system 100 may operate the pump at speeds such as 100 ml/min to 1000 ml/min respectively.

In some instances, it may be beneficial/necessary for the user to manually control the operation of the system 100 in order to determine the required parameters and determine how the protocol/algorithm should be created. In order to capture and create the protocol/algorithm from this manual mode, some embodiments may include a learning mode. When in this learning mode, the system 100 (e.g., the processor or controller) tracks the states, valve positions, pump speeds, processed volumes, other system parameters, and the manual operation of the device/system 100. Once the procedure is completed, the user may turn off the learning mode and the system may create a protocol/algorithm based on the states and parameters at which the device was run during the manual mode (e.g., when the learning/listening is on). Once the protocol is created, the user may save and/or edit the processing steps as needed. This, in turn, allows the user to reproducibly repeat the manual process just performed and allows users to capture a variable/long process with minimal button presses.

Some embodiments may also provide for process optimization which, in turn, allows deeper customization. For example, by utilizing the device monitoring instruments and sensors (e.g., the effluent sensors and bowl optics sensor), the system 100 may display the effluent signals obtained (Max, Min) during a state after running on actual product. This allows users to utilize these signal detections to change states. To optimize a given protocol, the user may first create/build the protocol as described above and then run the protocol (e.g., on actual product). The system 100 may then display the bowl optics and effluent signals across each state on the display 140. The user may then select thresholds for the end of a given state. If user wanted to fill the bowl 110 until a drop in the line sensor signal occurs (e.g., from a signal of 1800 A/D counts to target of 500 A/D counts), the user may select "500 effluent" in order to change from the fill cycle to the next subsequent cycle.

Although the embodiments discussed above create the custom protocols directly at the cell processing device 100, other embodiments may create the protocols remotely. For example, in some embodiments, the user creating the protocols may be located at a remote system (e.g., a remote server or computer system) that is in communication with one or more cell processing devices, for example, via a global data communication network such as the internet). Once created at the remote system, the remote system can send/transmit the created protocols to one or more of the cell processing devices to which it is in communication.

It should be also noted that terms such as "controller," "processor" and "server" may be used herein to describe devices that may be used in certain embodiments of the present invention and should not be construed to limit the present invention to any particular device type or system unless the context otherwise requires. Thus, a system may include, without limitation, a client, server, computer, appliance, or other type of device. Such devices typically include one or more network interfaces for communicating over a communication network and a processor (e.g., a microprocessor with memory and other peripherals and/or application-specific hardware) configured accordingly to perform device and/or system functions. Communication networks generally may include public and/or private networks; may include local-area, wide-area, metropolitan-area, storage, and/or other types of networks; and may employ communication technologies including, but in no way limited to, analog technologies, digital technologies, optical technologies, wireless technologies, networking technologies, and internetworking technologies The various components of the control program may be implemented individually or in combination. For example, each component may be implemented or a dedicated server or a set of servers configured in a distributed manner It should also be noted that devices may use communication protocols and messages (e.g., messages created, transmitted, received, stored, and/or processed by the system), and such messages may be conveyed by a communication network or medium. Unless the context otherwise requires, the present invention should not be construed as being limited to any particular communication message type, communication message format, or communication protocol. Thus, a communication message generally may include, without limitation, a frame, packet, datagram, user datagram, cell, or other type of communication message. Unless the context requires otherwise, references to specific communication protocols are exemplary, and it should be understood that alternative embodiments may, as appropriate, employ variations of such communication protocols (e.g., modifications or extensions of the protocol that may be made from time-to-time) or other protocols either known or developed in the future.

It should also be noted that logic flows may be described herein to demonstrate various aspects of the invention, and should not be construed to limit the present invention to any particular logic flow or logic implementation. The described logic may be partitioned into different logic blocks (e.g., programs, modules, interfaces, functions, or subroutines) without changing the overall results or otherwise departing from the true scope of the invention. Often times, logic elements may be added, modified, omitted, performed in a different order, or implemented using different logic constructs (e.g., logic gates, looping primitives, conditional logic, and other logic constructs) without changing the overall results or otherwise departing from the true scope of the invention.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other programmable logic device (PLD)), discrete components, integrated circuitry (e.g., an Application Specific Integrated Circuit (ASIC)), or any other means including any combination thereof. In some embodiments of the present invention, predominantly all of the described logic is implemented as a set of computer program instructions that is converted into a computer executable form, stored as such in a computer readable medium, and executed by a microprocessor under the control of an operating system.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as FORTRAN, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web). In fact, some embodiments, may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for creating a custom cell processing protocol comprising:

(a) providing a cell processing device, the cell processing device having a display, a blood component separation device, a plurality of valves, one or more sensors to detect one or more fluid levels, and a pump;

(b) performing a cell processing procedure on the cell processing device;

(c) manually controlling the operation of the cell processing device during the cell processing procedure;

(d) monitoring, using a processor within the cell processing device, the manual control of the operation of the cell processing device during the cell processing procedure; and (e) creating a custom protocol algorithm based, at least in part, on the monitored manual control of the operation of the cell processing device and including one or more modified phase parameters for the cell processing procedure, wherein the cell processing device performs a cell processing procedure based on the custom protocol algorithm to control operation of the blood component separation device and the pump and uses the one or more sensors to detect one or more fluid levels associated with the modified one or more phase parameters during the performance of the modified cell processing procedure.

2. A method according to claim 1, wherein manually controlling the operation of the cell processing device includes at least one selected from the group consisting of manual operation of at least one of the plurality of valves, manual operation of the pump speed, manual operation of process volumes, manual operation of the state the cell processing device is in, and manual operation of system parameters.

3. A method according to claim 1, further comprising saving the custom protocol algorithm in a data storage device.

4. A method according to claim 1, further comprising modifying the custom protocol algorithm.

5. A system for creating a custom cell processing protocol comprising:

a cell processing device configured to process blood and/or blood products, the cell processing device having a blood component separation device, a plurality of valves, one or more sensors to detect one or more fluid levels and a pump;

an interface located on the cell processing device and configured to allow a user to place the cell processing device into a learning mode, the user manually controlling the operation of the cell processing device during a cell processing procedure when in the learning mode; and a processor configured to monitor the manual control of the operation of the cell processing device during the cell processing procedure when in the learning mode, and generate a custom protocol algorithm that includes one or more modified phase parameters for the cell processing procedure based, at least in part on the monitored manual control of the operation of the cell processing device, wherein the cell processing device performs a cell processing procedure based on the custom protocol algorithm to control operation of the blood component separation device and the pump and uses the one or more sensors to detect one or more fluid levels associated with the modified one or more phase parameters during the performance of the modified cell processing procedure.

6. A system according to claim 5, wherein the manual control of the operation of the cell processing device includes at least one selected from the group consisting of manual operation of at least one of the plurality of valves, manual operation of the pump speed, manual operation of process volumes, manual operation of the state the cell processing device is in, and manual operation of system parameters.

7. A system according to claim 5, further comprising a data storage device configured to store the custom protocol algorithm.

8. A system according to claim 5, wherein the interface is further configured to allow a user to modify the custom protocol algorithm.

9. A system according to claim 5, wherein the cell processing device includes a controller, the controller configured to operate the cell processing device according to the custom protocol algorithm.

10. A system according to claim 9, wherein the controller is configured to control at least one selected from the pump, the blood component separation device, and at least one of the plurality of valves.

* * * * *